United States Patent
Yoshihara et al.

(10) Patent No.: US 6,806,224 B2
(45) Date of Patent: Oct. 19, 2004

(54) PROCESS FOR PRODUCING A SUPPORTED METAL CATALYST

(75) Inventors: Jun Yoshihara, Ibaraki (JP); Takashi Motoi, Ibaraki (JP); Kazuaki Maeshima, Ibaraki (JP)

(73) Assignee: Mitsubishi Gas Chemical Company, Inc., Tokyo (JP)

(*) Notice: Subject to any disclaimer, the term of this patent is extended or adjusted under 35 U.S.C. 154(b) by 73 days.

(21) Appl. No.: 10/113,574

(22) Filed: Apr. 2, 2002

(65) Prior Publication Data

US 2002/0151433 A1 Oct. 17, 2002

(30) Foreign Application Priority Data

Apr. 3, 2001 (JP) ........................................ 2001-104282

(51) Int. Cl.[7] .............................................. B01S 21/18
(52) U.S. Cl. ................... 502/185; 502/162; 502/164; 502/167; 502/169; 502/172; 502/184; 502/224; 502/230; 502/330
(58) Field of Search ................... 502/162, 164, 502/167, 169, 172, 184, 185, 224, 230, 330

(56) References Cited

U.S. PATENT DOCUMENTS

| | | | | |
|---|---|---|---|---|
| 4,212,854 A | | 7/1980 | Maki et al. ................ 423/247 |
| 4,533,772 A | * | 8/1985 | Michaelson et al. ........ 568/860 |
| 5,650,546 A | * | 7/1997 | Chaudhari et al. .......... 585/269 |
| 6,462,242 B1 | * | 10/2002 | Neugebauer et al. ....... 568/812 |
| 6,528,453 B2 | * | 3/2003 | Baker et al. ................ 502/325 |
| 6,534,438 B1 | * | 3/2003 | Baker et al. ................ 502/325 |
| 6,579,825 B2 | * | 6/2003 | Lockemeyer ............... 502/347 |
| 2003/0135009 A1 | * | 7/2003 | Chaudhari et al. ........... 528/48 |
| 2003/0139624 A1 | * | 7/2003 | Baker et al. ................ 560/243 |

FOREIGN PATENT DOCUMENTS

| | | |
|---|---|---|
| GB | 762728 | 12/1956 |
| GB | 844358 | 8/1960 |

OTHER PUBLICATIONS

European Search Report, dated Jul. 12, 2002, in EPA No. 02006971.

* cited by examiner

*Primary Examiner*—Mark L. Bell
*Assistant Examiner*—Patricia L. Hailey
(74) *Attorney, Agent, or Firm*—Antonelli, Terry, Stout & Kraus, LLP

(57) ABSTRACT

A process for producing a supported metal catalyst which comprises reducing a metal halide in the liquid phase in the presence of a support material, an organic base and a reducing agent. In accordance with the process, the supported metal catalyst which comprises a metal component supported in the highly dispersed condition and exhibits high activity can be obtained easily.

11 Claims, No Drawings

PROCESS FOR PRODUCING A SUPPORTED METAL CATALYST

BACKGROUND OF THE INVENTION

1. Field of the Invention

The present invention relates to a process for producing a supported metal catalyst which comprises a metal more highly dispersed than that in conventional supported catalysts.

2. Description of the Related Arts

As the process for producing a supported metal catalyst, a process in which an inert support material is impregnated with or allowed to adsorb a salt of a metal used as the catalyst, the metal salt is reduced by treating the resultant product with a reducing agent such as hydrogen gas and fine particles of the metal are formed on the surface of the support material, has been known. However, in accordance with this process, it is necessary that the treatment of reduction be conducted at a high temperature since the entire amount of the metal salt on the support material must be reduced into fine particles of the metal. The treatment at a high temperature causes sintering of the fine particles of the metal and, as the result, it is difficult that a catalyst in which the metal is highly dispersed is obtained.

As another process, a process in which colloidal particles of a metal dispersed in a liquid are fixed on a support material has been known. Since colloidal particles of a metal tend to aggregate with each other and precipitate, in general, a protective colloid is formed by adding a macromolecular compound or a surfactant so that the dispersion is stabilized. In general, for preparation of a supported metal catalyst using colloidal particles of a metal, the colloidal particles of a metal is stabilized as a protective colloid using the above method, then a support material is added to the stabilized colloidal fluid and the resultant colloidal fluid is destabilized by heating or the like method (for example, Japanese Patent Application Laid-Open No. Showa 56(1981)-155645). However, this process has drawbacks in that the process for the preparation requires many steps and that the amount of the metal supported on the support material decreases due to the stabilization of the colloid of the metal as the protective colloid by the addition of a macromolecular compound or a surfactant and the process is disadvantageous with respect to cost, in particular, When a supported noble metal catalyst is prepared.

As still another process for preparing a supported metal catalyst using a colloidal fluid, Nakao et al. introduced a process for supporting a metal without using a protective colloid (Japanese Patent Application Publication Heisei 3(1991)-60534). Although this process may be considered to be advantageous with respect to cost since no protective colloid is used, an expensive salt of boron hydride is used for reduction of the metal salt and this process is disadvantageous with respect to cost. Moreover, when an alkali metal salt of boron hydride which is most stable and most easily available among salts of boron hydride is used, the alkali metal component tends to remain in the catalyst and unexpected side reactions frequently take place in the actual reaction system. Therefore, the above process is not preferable.

For producing a supported metal catalyst in accordance with the so-called ion exchange process, the surface treatment of the support material, repeated exchange reactions of functional groups at the surface of the support material with the metal ion and the treatment of reduction must be conducted and it takes a long time for the preparation. Moreover, since the amount of the supported metal is limited by the ion-exchange capacity of the support material (Petrotech, Volume 17, 1994, Page 331), it is difficult that a supported metal catalyst having a great amount of the supported metal is prepared. The above process has a further drawback in that the obtained supported metal catalyst does not always exhibit a high activity since sintering of the metal particles occasionally takes place during the treatment of reduction.

As the process for producing a metal black, the process of Feulgen et al. has been known for a long time (Ber., 54, 360 (1921)). However, when the process of Feulgen et al. is applied to preparation of a supported metal catalyst, an alkali metal is mixed into the catalyst since an alkali metal compound is used in a step of the preparation. Therefore, this process is not preferable. When the obtained catalyst is washed with a great amount of water to remove the alkali metal, a drawback arises in that, since a portion of the metal intended to be supported on the support material flows away as colloidal particles, the metal is not fixed to the support material in the prescribed amount and the portion of the metal which has flowed away must be recovered.

SUMMARY OF THE INVENTION

The object of present invention is to provide an industrially advantageous process for producing a supported metal catalyst which comprises the metal component supported in the highly dispersed condition and exhibits high activity.

As the result of intensive studies by the present inventors to overcome the above drawbacks on the process for preparing a supported metal catalyst, it was found that a supported metal catalyst which comprises the metal component supported in the highly dispersed condition could be obtained by using an inexpensive metal halide as the raw material and reducing the metal component in the liquid phase in the presence of an organic base. The present invention has been completed based on this knowledge.

The present invention provides a process for producing a supported metal catalyst which comprises reducing a metal halide in a liquid phase in a presence of a support material, an organic base and a reducing agent.

DESCRIPTION OF THE PREFERRED EMBODIMENTS

In the process for producing a supported metal catalyst of the present invention, a metal halide is used as the precursor.

As the metal component, various metals which can be used as the catalyst can be used. Gold, silver, platinum, rhodium, palladium, ruthenium, osmium and iridium are preferable. The metal component is used as a halide such as fluoride, chloride, bromide and iodide.

The metal halide may be used singly or as a mixture of two or more. When a metal halide having poor solubility in water is used as the precursor, it is necessary that the metal halide is dissolved into a dilute hydrochloric acid or a dilute nitric acid so that an aqueous solution is prepared and the prepared aqueous solution is used for the process.

For producing a supported metal catalyst of the present invention, various support materials usually used for supported metal catalysts may be used. Examples of the support materials include carbon black, activated carbon, alumina and silica.

As the organic base used in the process for producing a supported metal catalyst of the present invention, quaternary ammonium hydroxides represented by general formula (1), quaternary ammonium hydroxides represented by general formula (2), tertiary alkylamines represented by general formula (3) and triethylenediamine (1,4-diazabicyclo[2,2,2]octane) are preferably used. The organic base may be used singly or as a mixture.

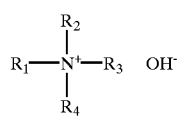

(1)

In general formula (1), $R_1$, $R_2$, $R_3$ and $R_4$ each represent an alkyl group having 1 to 4 carbon atoms.

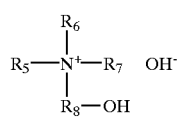

(2)

In general formula (2), $R_5$, $R_6$ and $R_7$ each represent an allyl group having 1 to 4 carbon atoms and $R_8$—OH represents a hydroxyalkyl group having 1 to 4 carbon atoms.

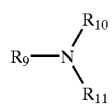

(3)

In general formula (3), $R_9$, $R_{10}$ and $R_{11}$ each represent an alkyl group having 1 to 6 carbon atoms.

Among the organic bases represented by the above general formulae, tetramethylammonium hydroxide, tetraethylammonium hydroxide, tetrapropylammonium hydroxide, tetrabutylammonium hydroxide and choline are preferable and tetramethylammonium hydroxide is more preferable.

When sodium hydroxide is used as the base without using the organic base, the supported metal flows away as a colloid during washing of the obtained catalyst to remove the alkali metal and a catalyst having the metal in the desired amount cannot be obtained. When ammonia is used as the base, a stable ammine complex is formed and the metal cannot be supported on the support material when some types of the metal are used.

In the process for producing a supported metal catalyst of the present invention, the amount of the organic base used in the process relative to the amount of the metal halide is in the range of 2 to 15 equivalents and preferably in the range of 3 to 12 equivalents per 1 equivalent of the metal halide. When the organic base is added to a metal halide having poor solubility in water, it is necessary that the amount of the organic base be increased by the amount required for neutralizing a dilute hydrochloric acid or a dilute nitric acid which is used for dissolving the metal halide. When the amount of the organic base is smaller than 2 equivalents per 1 equivalent of the metal halide, reduction of the metal halide does not proceed sufficiently and the fraction of the metal supported on the support material decreases. Therefore, the catalyst having the desired amount of the supported metal cannot be obtained. Moreover, the decrease in the fraction of the metal successfully supported on the support material is disadvantageous with respect to cost since the amount of the lost metal is great. When the amount of the organic base exceeds 15 equivalents per 1 equivalent of the metal halide, the liquid frequently becomes markedly basic during the preparation and, occasionally, portions of the base and the metal form stable complex compounds. Since these complex compounds are not supported on the support material, the catalyst having the desired amount of the supported metal cannot be obtained. Therefore, such range of amount of organic base is not preferable.

Alcohols, aqueous solutions of formaldehyde and of hydrazine hydrate may be used as the reducing agent in the process for producing a supported metal catalyst of the present invention. Among them, the aqueous solutions of formaldehyde are more preferable. Examples of the alcohol include methanol, ethanol, n-propyl alcohol, isopropyl alcohol, n-butyl alcohol, sec-butyl alcohol and isobutyl alcohol.

In the process for producing a supported metal catalyst of the present invention, the amount of the reducing agent used in the process relative to the amount of the metal halide is in the range of 1 to 6 equivalents per 1 equivalent of the metal halide. When the amount of the reducing agent is smaller than 1 equivalent per 1 equivalent of the metal halide, reduction of the metal halide does not proceed sufficiently and the fraction of the metal supported on the support material decreases. Therefore, the catalyst having the desired amount of the supported metal cannot be obtained. Moreover, the decrease in the fraction of the metal successfully supported on the support material is disadvantageous with respect to the cost. When the amount of the reducing agent exceeds 6 equivalents per 1 equivalent of the metal halide, the specific surface area of the metal in the obtained catalyst is small. Therefore, such amount of reducing agents is not preferable. However, when the above alcohol used as the reducing agent is also used as the solvent described in the following, the alcohol may be used in an amount outside the above range.

The preparation of the supported metal catalyst in accordance with the present invention is performed in the liquid phase. Water is mainly used as the solvent. Alcohols such as methanol, ethanol, n-propyl alcohol, isopropyl alcohol, n-butyl alcohol, sec-butyl alcohol, isobutyl alcohol and tert-butyl alcohol can also be used as the solvent. The solvent may be used as a mixture of two or more.

The preparation of the supported metal catalyst is conducted at a temperature in the range of 5 to 120° C. and preferably in the range of 5 to 100° C. When the temperature is lower than 5° C., reduction of the metal halide does not proceed sufficiently and the fraction of the metal supported on the support material decreases. Therefore, the catalyst having the desired amount of the supported metal cannot be obtained. Moreover, amount of the metal lost will be large, making the process less feasible with respect to the cost of production. When the temperature exceeds 120° C., the vaporized amounts of the organic base and the reducing agent during the preparation increase and the reduction of the metal salt does not proceed sufficiently. Therefore, such temperature range is not preferable.

In the process for producing a supported metal catalyst of the present invention, the concentration of the metal halide in the solvent used in the preparation of the catalyst is that the metal component of the metal halide in the range of 0.1 to 5% by weight as a metal and preferably in the range of 0.5 to 2.5% by weight. When the concentration of the metal component of the metal halide in the solvent is smaller than 0.1% by weight, the metal is not sufficiently supported on the support material and such a concentration is not preferable. When the concentration of the metal component of the metal halide in the solvent exceeds 5% by weight as a metal, the dispersion of the metal on the support material in the obtained catalyst becomes poor and such a concentration is not preferable.

In accordance with the present invention, the supported metal catalyst which comprises the metal component supported in the highly dispersed condition and exhibits high activity can be obtained easily. In general, when a catalyst which comprises a large amount of a supported metal is prepared, it is difficult that the metal component is supported in a highly dispersed form. Even in such a case, the supported metal catalyst which comprises a metal component supported in the highly dispersed condition and exhibits high activity can be obtained easily in accordance with the present invention.

The supported metal catalyst prepared in accordance with the process of the present invention can exhibit the above advantageous effect independently of the amount of the supported metal component. Since the specific surface area of the metal is large, the amount of the catalyst used as the catalyst can be decreased to a great extent and the process is advantageous with respect to the cost.

EXAMPLES

The present invention will be described more specifically with reference to examples in the following. However, the present invention is not limited to these examples.

Example 1

10.5 g of carbon black was placed into a 500 ml flask and dispersed in 240 g of water. Then, 12.2 g of hexachloroplatinic(IV) acid hydrate, 9.2 g of an aqueous solution of 36% by weight formaldehyde and 80 g of an aqueous solution of 25% by weight tetramethylammonium hydroxide were added. The temperature of the resultant mixture was raised to 95° C. under stirring and the reaction was allowed to proceed at 95° C. for 1 hour. Then, the resultant slurry was filtered and washed with water. The residue obtained after the washing was dried by heating under a reduced pressure and a carbon black-supported platinum catalyst containing 30% by weight of platinum was obtained. The filtrate obtained after the filtration was analyzed and no platinum was detected Therefore, the entire amount of platinum contained in the hexachloroplatinic(IV) acid hydrate used for the preparation of the catalyst was supported on the carbon black. The obtained carbon black-supported platinum catalyst was observed by using a transmission electron microscope. The particles of the platinum had diameters in the range of 4 to 5 nm and were supported on the carbon black in a highly dispersed form. The surface area of platinum per unit weight in the obtained supported metal catalyst was measured in accordance with the CO adsorption method and found to be 97 $m^2/g$.

Example 2

10.5 g of carbon black was placed into a 200 ml flask and dispersed in 100 g of water. Then, 0.28 g of hexachloroplatinic (IV) acid hydrate, 0.2 g of an aqueous solution of 36% by weight formaldehyde and 2.0 g of an aqueous solution of 25% by weight tetramethylammonium hydroxide were added. The temperature of the resultant mixture was raised to 95° C. under stirring and the reaction was allowed to proceed at 95° C. for 1 hour. Then, the resultant slurry was filtered and washed with water. The residue obtained after the washing was dried by heating under a reduced pressure and a carbon black-supported platinum catalyst containing 1% by weight of platinum was obtained. The filtrate obtained after the filtration was analyzed and no platinum was detected. Therefore, the entire amount of platinum contained in the hexachloroplatinic(IV) acid hydrate used for the preparation of the catalyst was supported on the carbon black. The surface area of platinum per unit weight in the obtained supported metal catalyst was measured in accordance with the CO adsorption method and found to be 208 $m^2/g$.

Example 3

10.5 g of carbon black was placed into a 500 ml flask and dispersed in 240 g of water. After an aqueous solution prepared by dissolving 7.9 g of palladium chloride in 20 ml of 1 N hydrochloric acid was added, 9 g of an aqueous solution of 36% by weight formaldehyde and 107 g of an aqueous solution of 25% by weight tetramethylammonium hydroxide were added. The temperature of the resultant mixture was raised to 95° C. under stirring and the reaction was allowed to proceed at 95° C. for 1 hour. Then, the resultant slurry was filtered and washed with water. The residue obtained after the washing was dried by heating under a reduced pressure and a carbon black-supported palladium catalyst containing 31% by weight of palladium was obtained. The filtrate obtained after the filtration was analyzed and no palladium was detected. Therefore, the entire amount of palladium contained in palladium chloride used for the preparation of the catalyst was supported on the carbon black. The surface area of palladium per unit weight in the obtained supported metal catalyst was measured in accordance with the CO adsorption method and found to be 70 $m^2/g$.

Comparative Example 1

10.5 g of carbon black was placed into a 500 ml flask and dispersed in 140 g of water. Then, 12 g of hexachloroplatinic (IV) acid hydrate, 10 g of an aqueous solution of 36% by weight formaldehyde and 81 g of an aqueous solution of 25% by weight sodium hydroxide were added. The temperature of the resultant mixture was raised to 95° C. under stirring and the reaction was allowed to proceed at 95° C. for 1 hour. Then, the resultant slurry was filtered. Platinum flowed away as a colloid and the desired platinum catalyst supported on the carbon black could not be obtained.

Example 4

9.9 g of carbon black was placed into a 200 ml flask and dispersed in 60 g of water. After an aqueous solution prepared by dissolving 0.17 g of palladium chloride into 5 ml of 1 N hydrochloric acid was added to the resultant solution, 0.2 g of an aqueous solution of 36% by weight formaldehyde and 4.0 g of an aqueous solution of 25% by weight tetramethylammonium hydroxide were added. The temperature of the resultant mixture was raised to 95° C. under stirring and the reaction was allowed to proceed at 95° C. for 1 hour. Then, the resultant slurry was filtered and washed with water. The residue obtained after the washing was dried by heating under a reduced pressure and a carbon black-supported palladium catalyst containing 1% by weight of palladium was obtained. The filtrate obtained after the filtration was analyzed and no palladium was detected. Therefore, the entire amount of palladium contained in palladium chloride used for the preparation of the catalyst was supported on the carbon black. The surface area of palladium per unit weight in the obtained supported metal catalyst was measured in accordance with the CO adsorption method and found to be 192 m²/g.

Application Example 1

Using the carbon black-supported palladium catalyst containing 1% by weight of palladium which was prepared in Example 4, benzaldehyde was hydrogenated to synthesize benzyl alcohol.

Into a 100 ml autoclave, 0.17 g of the carbon black-supported palladium catalyst containing 1% by weight of palladium which was, prepared in Example 4, 6.7 g of benzaldehyde and 27 g of ethanol as the solvent were placed. After the autoclave was filled with hydrogen in an amount such that the inner pressure of the autoclave was 2.5 MPa at the room temperature, the reaction was allowed to proceed at 80° C. for 30 minutes. The obtained resultant fluid was analyzed and the conversion of benzaldehyde was found to be 87%.

Comparative Application Example 1

Into a 200 ml flask, 0.17 g of palladium chloride was dissolved into 5 ml of a 1 N hydrochloric acid. Then, 90 g of water was added to the resultant solution and a uniform solution was obtained. To the obtained solution, 9.9 g of carbon black was added and the resultant mixture was stirred for 30 minutes. While the obtained fluid was stirred, water was removed by distillation by reducing the pressure in the flask and the palladium component was supported on the carbon black. After the content of the flask was taken out and dried in vacuo for 2 hours, the dried product was reduced under a hydrogen stream at 300° C. for 2 hours and a carbon black-supported palladium catalyst containing 1% by weight of palladium was obtained.

Using the carbon black-supported palladium catalyst containing 1% by weight of palladium which was prepared above in accordance with the impregnation process, benzaldehyde was hydrogenated and benzyl alcohol was synthesized. The reaction was conducted under the same condition as that in Application Example 1. The obtained resultant fluid was analyzed and the conversion of benzaldehyde was found to be 68%.

What is claimed is:

1. A process for producing a supported metal catalyst which comprises reducing a metal halide in a liquid phase in a presence of a support material, an organic base and a reducing agent, wherein the organic base is at least one compound selected from the group consisting of tetramethylammonium hydroxide, tetraethylammonium hydroxide, tetrapropylammonium hydroxide, tetrabutylammonium hydroxide and choline.

2. A process according to claim 1, wherein the metal halide is at least one metal halide selected from the group consisting of halides of gold, silver, platinum, rhodium, palladium, ruthenium, osmium and iridium.

3. A process according to claim 2, wherein the halide is selected from the group consisting of fluoride, chloride, bromide and iodide.

4. A process according to claim 1, wherein the reducing agent is at least one compound selected from the group consisting of alcohols, aqueous solutions of formaldehyde and aqueous solutions of hydrazine hydrate.

5. A process according to claim 1, wherein the metal halide is reduced in a liquid phase at 5 to 120° C. using water, an alcohol or a mixture thereof as a solvent.

6. A process according to claim 1, wherein the halide is selected from the group consisting of fluoride, chloride, bromide and iodide.

7. A process according to claim 1, wherein, prior to the reducing, the metal halide is dissolved in dilute hydrochloric acid or dilute nitric acid.

8. A process according to claim 7, wherein amount of the organic base used in the process is a sum of amount thereof to neutralize the dilute hydrochloride acid or dilute nitric acid plus 2 to 15 equivalents per 1 equivalent of the metal halide.

9. A process according to claim 1, wherein said organic base is tetramethylammonium hydroxide.

10. A process according to claim 1, wherein amount of organic base used in the process is 2 to 15 equivalents per 1 equivalent of the metal halide.

11. A process according to claim 10, wherein amount of the reducing agent used in the process is 1 to 6 equivalents per 1 equivalent of the metal halide.

* * * * *